United States Patent [19]

Haugland et al.

[11] Patent Number: 5,132,432
[45] Date of Patent: Jul. 21, 1992

[54] CHEMICALLY REACTIVE PYRENYLOXY SULFONIC ACID DYES

[75] Inventors: Richard P. Haugland; James E. Whitaker, both of Eugene, Oreg.

[73] Assignee: Molecular Probes, Inc., Eugene, Oreg.

[21] Appl. No.: 410,837

[22] Filed: Sep. 22, 1989

[51] Int. Cl.$^5$ ............... C07C 247/24; C07C 309/38; C01D 207/36; G01N 22/00
[52] U.S. Cl. ................ 548/518; 548/528; 548/543; 552/6; 562/45; 562/46; 562/47; 562/55; 8/648; 436/172
[58] Field of Search ............ 562/45, 46, 47, 55; 548/518, 543, 528; 560/10; 552/6; 558/46, 6, 17; 436/172; 8/648

[56] References Cited

U.S. PATENT DOCUMENTS

| | | | |
|---|---|---|---|
| 2,122,828 | 7/1938 | Wiegand et al. | 562/47 |
| 3,996,345 | 12/1976 | Ullman et al. | 530/363 |
| 4,213,904 | 7/1980 | Haugland | 544/212 |
| 4,520,110 | 5/1985 | Stryer et al. | 530/370 |
| 4,542,104 | 9/1985 | Stryon et al. | 436/537 |
| 4,844,841 | 7/1989 | Koller et al. | 562/55 |

OTHER PUBLICATIONS

Baker and Collis, "Fluorescent Acylating Agents Derived From 7-Hydroxycoumarin," *J. Chem. Soc.* (1949) S12-S15.

Barzilay et al., "Anion Transport in Red Blood Cells I. Chemical Properties of Anion Recognition Sites as Revealed by Structure-Activity Relationships of Aromatic Sulfonic Acids," *Membr. Biochem.* 2:227-254 (1979).

Braunitzer et al., "Zur Vollstandigen Automatischen Sequenzanalyse von Peptiden mit Quadrol," *Hoppe-Seyler's Z. Physiol. Chem.* 352:1730-1732 (1971).

Coons and Kaplan, "Localization of Antigen in Tissue Cells II. Improvements in a Method for the Detection of Antigen by Means of Fluorescent Antibody," *J. Exp. Med.* 91:1 (1950).

Cornelisse and Ploem, "A New Type of Two-Color Fluorescence Staining for Cytology Specimens," *J. Histochem. and Cytochem.* 24:72-81 (1976).

(List continued on next page.)

*Primary Examiner*—Mukund J. Shah
*Assistant Examiner*—Edward C. Ward

[57] ABSTRACT

The invention relates to novel fluorescent dyes based on the following pyrenyloxy sulfonic acid structure:

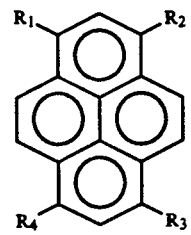

wherein at least one of $R_1$, $R_2$, $R_3$, and $R_4$ is —OCH$_2$C(O)OCH$_3$, —OCH$_2$CON(O)H, —OCH$_2$CON$_3$, —OCH$_2$CONHNH$_2$,

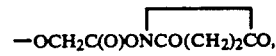

or —CH$_2$CONH(CH$_2$)$_n$NH$_2$ where n is an integer from 1 to 10; at least one of $R_1$, $R_2$, $R_3$, and $R_4$ is sulfonic acid or alkali salts of sulfonic acid; and all other of $R_1$, $R_2$, $R_3$, and $R_4$ are hydrogen or a hydroxyl group. The new reagents contain functional groups typically found in biomolecules or polymers. The spectral properties of the fluorescent dyes are sufficiently different in wavelengths and intensity from fluorescein as to permit simultaneous use of both dyes with minimum interference. The dyes have narrower spectral band-widths and smaller Stokes' shifts than other reactive dyes with similar spectral properties, do not show appreciable sensitivity to pH, have higher solubilities in aqueous solvents and have good quantum yields and photostability.

9 Claims, 5 Drawing Sheets

Absorption spectrum of 12.

OTHER PUBLICATIONS

Khalfan et al., "Fluorigenic Method for the Assay of Proteinase Activity With the Use of 4-Methylumbelliferyl-casein," *Biochem. J.* 209:265-267 (1983).

Khalfan et al., "Aminomethyl Coumarin Acetic Acid: A New Fluorescent Labelling Agent for Proteins," *Histochem. J.* 18:497-499 (1986).

Lutty, "The Acute Intravenous Toxicity of Biological Stains, Dyes, and Other Fluorescent Substances," *Toxicol. and Appl. Pharmacol.* 44:225-249 (1978).

Riggs et al., "Isothiocyanate Compounds as Fluorescent Labeling Agents for Immune Serum," *Amer. J. Path.* 34:1081-1092 (1958).

Smith et al., "The Synthesis of Oligonucleotides Containing an Aliphatic Amino Group at the 5' Terminus: Synthesis of Fluorescent DNA Primers for Use in DNA Sequence Analysis," *Nucl. Acids Res.* 13:2399-2412 (1985).

Smith et al., "Fluorescence Detection in Automated DNA Sequence Analysis," *Nature* 321:674-679 (1986).

Speth and Schulze, "On the Nature of the Interaction Between 4,4'-Diisothiocyanostilbene 2,2'-Disulfonic Acid and Microsomal Glucose-6-Phosphatase," *Eur. J. Biochem.* 174:111-117 (1988).

Staines et al., "Three-Color Immunofluorescence Histochemistry Allowing Triple Labeling Within a Single Section," *J. Histochem. and Cytochem.* 36:145-151 (1988).

Cooper, Spectroscopic Techniques for Organic Chemists [New York, J. Wiley, 1980,] pp. 240 to 243.

Titus, et al. J. Immunological Methods 50 (1982) 193-204.

Lanier, et al. J. of Immunology 132(1) 1984 pp. 151 to 156.

Kanaoka Angew. Chem. 16 137-147 1977 Weber Biochem. J. 51, 145 (1952).

Bassi, et al. Expermentia vol. XVI 430, 1960 Rinderknecht, Expermentia 16, 430, 1960.

Jolley, et al. Clinical Chemistry, 27/7, 1981 pp. 1190-1197.

Hemmila, Clinical Chemistry 31/3, 1985 359-370.

Braunitzer et al., Hoppe-Seyler's Z. Physiologik Chemie. Dec. 1973, pp. 1563-1566.

Malencik et al. Biochemistry, vol. 11,(16) 1972 pp.3022-3027.

Wolfbeis, Fresenius Z Anal. Chemie, 320 (271-273) 1985.

Khalaf et al. Hoppe-Seyler's, Physiol. Chemie 358, 1977, pp. 505-511.

CHEMICALLY REACTIVE PYRENYLOXY SULFONIC ACID DYES

FIELD OF THE INVENTION

This invention is related to improvements in dyes useful as fluorescent tracers. Specifically the improvements relate to chemically reactive dyes that can be attached to ligands with fluorescence properties sufficiently different from fluorescein derivatives that they can be selectively detected in the presence of fluorescein and have other unique spectral and chemical advantages.

BACKGROUND OF THE INVENTION

Fluorescent dyes are widely used as tracers for localization of biological structures by fluorescence microscopy, for quantification of analytes by fluorescence immunoassay, for flow cytometric analysis of cells, for measurement of physiological state of cells and other applications [Kanaoka Angew. Chem. Intl. Ed. Engl. 16:137 (1977); Hemmila, Clin. Chem. 31:359 (1985)]. Their primary advantages over other types of absorption dyes include the visibility of emission at a wavelength distinct from the excitation, the orders of magnitude greater detectability of fluorescence emission over light absorption, the generally low level of fluorescence background in most biological samples and the measurable intrinsic spectral properties of fluorescence polarization [Jolley, et al. Clin. Chem. 27:1190 (1981)], lifetime [U.S. Pat. No. 4,374,120] and excited state energy transfer [U.S. Pat. Nos. 3,996,345; 4,542,104].

For many applications that utilize fluorescent dyes as tracers, it is necessary to chemically react the dye with a biologically active ligand such as a cell, tissue, protein, antibody, enzyme, drug, hormone, nucleotide, nucleic acid, polysaccharide, lipid or other biomolecule to make a fluorescent ligand analog or to react the dye with natural or synthetic polymers. With these synthetic probes, the biomolecule frequently confers a specificity for a biochemical interaction that is under investigation and the fluorescent dye provides the method for detection and/or quantification of the interaction. Chemically reactive synthetic fluorescent dyes have long been recognized as essential for following these interactions [Soini & Hemmila, Clin. Chem. 25:353 (1979)]. It is also frequently desirable to employ more than one fluorescent conjugate simultaneously and to quantify the conjugates independently, requiring selective detection of each fluorescent probe. The dyes in common use are limited to a relatively small number of aromatic structures. It is an object of this invention to provide improved fluorescent dyes which have high water solubility. It is also an object of this invention to provide fluorescent tracers which can be used in conjunction with fluorescein and other commonly used fluorescent probes. It is further an object of this invention to provide dyes with the chemical reactivity necessary for conjugation to the functional groups commonly found in biomolecules, drugs, and natural and synthetic polymers. It is further an object of this invention to provide dyes whose fluorescence has low sensitivity to solution pH.

Coons and Kaplan [J. Exp. Med. 91:1 (1950)] first prepared a chemically reactive isocyanate of fluorescein and later Riggs, et al. [Am. J. Pathol. 34:1081 (1958)] introduced the more stable isothiocyanate analog of fluorescein. Fluorescein isothiocyanate (FITC) remains one of the most widely used tracers for fluorescent staining and immunoassay. Other reactive fluoresceins were prepared by Haugland [U.S. Pat. No. 4,213,904]. Virtually all fluorescence microscopes are equipped with excitation sources and filters optimized to excite and detect fluorescein emission. Fluorescein has broad emission in the visible portion of the spectrum beginning at approximately 480 nm, peaking at about 514 nm and decreasing to 10% of the peak intensity at approximately 580 nm.

The primary advantages that have permitted fluorescein isothiocyanate and its conjugates to remain the standard for microscopy and fluorescence immunoassay are a high absorbance, a high quantum yield and general ease of conjugation to biomolecules. Fluorescein has also become the predominant dye for use in the technique of flow cytometry [Lanier & Loken, J. Immunol. 132:151 (1984)].

There is a recognized need for suitable fluorophores for applications in multi-color microscopy [Khalfan, et al. (1986)], flow cytometry [Stryer, et al., U.S. Pat. No. 4,520,110; Titus, et al., J. Immunol. Methods 50:193 (1982)], immunoassays [Staines, et al., J. Histochem. Cytochem. 36:145 (1988)], and DNA sequencing [Smith, et al., Nature 321:674 (1986)]. Most of the dyes proposed for these applications have had longer wavelength emission than fluorescein. Since fluorescein has essentially no fluorescence below 490 nm, there is a clear opportunity to detect suitable fluorophores that have strong emission below this wavelength. The desirable dyes would have the following properties:

1. A high fluorescence quantum yield with a narrow emission peak at wavelengths sufficiently shorter than that of fluorescein so that the longest wavelength components of the dye emission have little or no spectral overlap with the fluorescein emission band.
2. A high absorptivity as measured by extinction coefficient. Preferred are dyes that can be excited with the most intense emission lines of the common excitation sources such as the 365 nm line of the mercury arc lamp. Excitation below 365 nm is less desirable since it can result in cell injury or death in applications where fluorescence measurements are performed on living cells. Furthermore, autofluorescence of proteins, nucleic acids and other biomolecules present in cells (especially NADH which has peak absorbance at 340 nm and peak emission at 460 nm) is also increased with shorter wavelength excitation. Use of wavelengths longer than 350 nm also permits use of less expensive glass optics instead of quartz optics.
3. High solubility of the dye and its reactive derivatives in aqueous solution to enhance the utility of the dye for modification of cells and biopolymers.
4. High stability of the dye to excitation light, enhancing the utility of the dye for quantitative measurements and permitting extended illumination time and higher lamp intensities for increased sensitivity.
5. For quantitative measurements, low sensitivity of the emission intensity to properties of the solution is necessary so that the measured signal is proportional only to the absolute quantity of dye present and is independent of environmental effects such as pH, viscosity and polarity.

6. Suitability of the dye for preparation of reactive derivatives of several different types which exhibit reactivity toward a variety of chemically reactive sites.

7. Intrinsically low biological activity or toxicity of the dye.

A number of dyes have been proposed in the literature that can be excited and detected at wavelengths less than 500 nm. Several chemically reactive fluorophores that can be excited in the near ultraviolet and short wavelength visible region of the spectrum have been described. The spectral properties and relative water solubilities of representative examples of these dyes and compound 12 of this invention are compared in Table 1. Undesirable properties of these dyes are indicated with an asterisk. These proposed tracers are derived from naphthalene derivatives such as 5-dimethylaminonaphthalene-1-sulfonic acid (Dansyl) [Weber, Biochem. J. 41:145 (1952); Rinderknecht, Experientin 16:430 (1960)], 3-(isothiocyanato)naphthalene-1,5-disulfonic acid [Braunitzer, et al., Hoppe-Seyler's Z. Physiol. Chem. 352:1730 (1971)] and N-(4-methylphenyl)-5-isothiocyanato-1,8-naphthalimide [Khalaf & Rimpler, Hoppe-Seyler's Z. Physiol. Chem. 358:505 (1977)], pyrene derivatives such as pyrene-1-butyric acid (PBA) [Malencik & Anderson, Biochemistry 11:3022 (1972)], 8-isothiocyanatopyrene-1,3,6-trisulfonic acid (IPTS) [Braunitzer, et al., Hoppe-Seyler's Z. Physiol. Chem. 354:1536 (1973)] and 8-hydroxypyrene-1,3,6-trisulfonyl chloride [Wolfbeis, Fresenies Z. Anal. Chem. 320:271 (1985)], stilbene derivatives such as 4-acetamido-4'-isothiocyanatostilbene-2,2'-disulfonic acid (SITS) [Cornelisse & Ploem, J. Histochem. Cytochem. 24:72 (1976)], and coumarin dyes such as 3-carboxy-7-hydroxycoumarin [Baker & Collis, J. Chem. Soc. 1949, S 12 (1949)], 7-hydroxy-4-methylumbelliferone-3-acetic acid (4-MUA) [Khalfan, et al., Biochem. J. 209:265 (1983)], 7-amino-4-methylcoumarin-3-acetic acid (AMCA) [Khalfan, et al., Histochem. J. 18:497 (1986)] and 7-diethylaminocoumarin [Staines, et al. (1988)].

The existing, reactive, blue-fluorescent fluorophores generally have much weaker absorptivity (extinction coefficients of less than 20,000 cm$^{-1}$ M$^{-1}$ at their absorbance maxima versus greater than 25,000 cm$^{-1}$ M$^{-1}$ for the compounds of this invention and 75,000 cm$^{-1}$ M$^{-1}$ for fluorescein at its peak near 490 nm) or lower quantum yields or lower solubility in aqueous solutions than the compounds described in this invention. Many important biological applications of fluorescence exist only in aqueous solution. Most importantly, the large Stokes' shifts and wide emission band-widths of several of these dyes result in significant residual fluorescence background from the ultraviolet excited dyes at wavelengths typically used for detection of fluorescein emission (typically 515 to 525 nm). The subject dyes have uniquely low background fluorescence at the wavelengths of the fluorescein emission maximum. With the exception of 4-MUA, the potential alternative dyes are not optimally suited for excitation with the strongest emission lines of the most commonly available sources, such as the 365 nm line of the mercury arc lamp. Fluorescence of several of the dyes that are potential alternatives to the dyes of the subject invention is frequently quenched in aqueous solution, resulting in low quantum yields. The lower quantum yield decreases the detection sensitivity or requires use of disproportionately larger quantities of the less fluorescent dye.

TABLE 1

| Dye | Abs Max. (nm) | ε (10$^{-3}$ M$^{-1}$cm$^{-1}$) | Em. Max. (nm) | Emission Bandwidth$^a$ (nm) | Emission Bandwidth$^a$ [cm$^{-1}$] | % Emission at 514 nm$^b$ (% of max) | Water Solubility$^c$ | Quantum Yield$^d$ |
|---|---|---|---|---|---|---|---|---|
| 4-MUA | 360 | 19.1* | 454 | 58 | [2668] | 20* | low* | med. |
| AMCA | 354 | 15.2* | 442 | 57 | [2858] | 12* | low* | med. |
| SITS | 337* | 37.4 | 438 | 82 | [4825]* | 19* | high | low* |
| Dansyl$^e$ | 340* | 4.5* | 578*$^e$ | —$^e$ | | —$^e$ | low* | low* |
| PBA | 341* | 45.1 | 377* | —$^f$ | | 2 | low* | low* |
| IPTS | 373 | 25.6 | 458 | 78 | [3634]* | 38* | high | low* |
| 12 | 399 | 28.0 | 423 | 50 | [2168] | 3.8 | high | high |
|  | 376 | 23.3 | | | | | | |

*These are undesirable properties of the dyes.
$^a$Full band-width at half peak height
$^b$Percent of maximum emission at 514 nm
$^c$Solubility of the reactive form of the dye
$^d$In aqueous solution
$^e$The spectral properties of dansyl derivatives are very sensitive to environmental effects
$^f$Alkylpyrene derivatives show multiple emission peaks Despite their acceptance as fluorescent tracers, coumarin derivatives have some deficiencies that preclude or make more difficult some useful applications. The reactive derivatives of aminocoumarins are quite lipophilic and insoluble in aqueous preparations. Additionally, hydroxycoumarin derivatives typically exhibit pK$_a$ values near or above 7.0 and show a pH dependent absorption spectrum which decreases the fluorescence yield of the fluorophore in the physiological pH range. The subject fluorophores have low sensitivity to the pH of the solution. This property is advantageous in the quantitative determination of fluorescence, where it is desirable to minimize the number of corrections which must be included in the calibration. Potential alternative dyes such as hydroxypyrenetrisulfonyl chloride and 4-MUA have high sensitivity to solution pH in the physiological range (pH 6 to 8).

While having other desirable properties of high absorbance and high water solubility, SITS has a very low fluorescence yield in water and is photolytically isomerized to the non-fluorescent cis isomer. Despite the commericial availability of SITS for over 15 years, use of SITS to form fluorescent conjugates has not been widely adopted due to the low fluorescence yield. SITS and related stilbene derivatives also have been found to have an inhibitory effect on anion transport systems in red blood cells [Barzilay, et al., Membrane Biochemistry 2:227 (1979)] and on microsomal glucose-6-phosphatase [Speth & Schulze, Eur. J. Biochem. 174:111 (1988)]. Another drawback of SITS is the short wavelength absorption maximum (<350 nm). Ultraviolet excitation can result in cell injury and death in applications where fluorescence measurements are performed on living cells. Autofluorescence of proteins, nucleic acids and other biomolecules present in cells is also increased with shorter wavelength excitation.

Furthermore, the emission spectra of stilbene, napthalene and coumarin derivatives have a very broad long wavelength component which greatly increases the fluorescence background at wavelengths used for detection of other dyes such as fluorescein, Lucifer Yellow and tetramethylrhodamine in applications such as DNA sequencing, developmental tracers and flow cytometry that require detection of multiple dyes and dye conjugates.

With the exception of SITS and the isothiocyanate of pyrenetrisulfonic acid, the solubility in aqueous solution of the commonly used reactive forms of these dyes is very low, necessitating use of organic solvent co-mixtures in forming dye conjugates with most biopolymers. Reactive dye derivatives such as succinimidyl pyrene-1-butyrate and the succinimidyl ester of AMCA are quite lipophilic and insoluble in the aqueous solutions which are required for fluorescent labelling of proteins, polysaccharides and other biomolecules.

The high ionic charge of the pyrenyloxy sulfonic acid dyes that are the subject of this invention results in fluorescent derivatives that are highly water soluble. The ionic charge and general lack of solubility in non-polar solvents of the subject dyes enhance their usefulness as fluorescent tracers for hydrophilic environments and increase their suitability for use in applications requiring neural and developmental tracers. This property also facilitates the coupling, in aqueous solution, of the fluorescent dye and a protein, drug, or other ligand of interest. Another potential advantage is the low toxicity of closely related compounds such as 8-hydroxy-pyrene-1,3,6-trisulfonic acid, which has been reported to have an $LD_{50}$ exceeding 1000 mg/kg [Lutty, Toxicol. Appl. Pharmacol. 44:225 (1978)].

In conclusion, the dyes which are the subject of this invention exhibit all of the desirable properties described above, namely:
1. Small Stokes' shifts, narrow emission bands and little spectral overlap with fluorescein.
2. High extinction coefficients, quantum yields and photostabilities.
3. High water solubility.
4. Low sensitivity to pH.
5. Reactivity with many of the functional groups found in biomolecules.
6. Compatibility with common excitation sources.

SUMMARY OF THE INVENTION

No fluorescent tracers have previously been described with the combination of pyrene, stilbene, naphthalene, or coumarin-like spectra, relatively high extinction coefficients and quantum efficiencies, little spectral overlap with fluorescein, chemical reactivity with the functional groups typically combined with fluorescent tracers, lack of pH sensitivity of spectra, narrow emission band-width and high solubility in aqueous environments.

The subject materials of this invention have fluorescence properties sufficiently different from fluorescein that they can be used concurrently with fluorescein-based tracers. They show low sensitivity of fluorescence emission to pH and solvent and have emission quantum yields which are typically greater than 0.5 and sometimes greater than 0.9 for a number of the subject compounds. The emission band-widths are narrower than those of coumarin, stilbene and naphthalene derivatives. These reactive derivatives possess multiple ionic charge and their reactive forms and conjugates have excellent solubility in water and other highly polar solvents.

DESCRIPTION OF SPECIFIC EMBODIMENTS

The base for the improved, reactive, hydrophilic fluorophores is a new pyrenyloxy sulfonic acid compound. The parent hydroxyl compound commonly was 8-hydroxypyrene-1,3,6-trisulfonic acid, trisodium salt (also called pyranine, Solvent Green 7, or D&C Green No. 8) which has been reported to be nontoxic to Swiss-Webster mice [Lutty (1978)]. Additional examples derived from 6,8-dihydroxypyrene-1,3-disulfonic acid, disodium salt are also described as an illustration of some of the modifications which are considered to fall within the scope of this invention. This invention describes methods for the synthesis of novel derivatives from this fluorophore and related pyrene derivatives as well as demonstration that the materials can be chemically bonded to the functional groups present in many biomolecules to form fluorescent ligand analogs or polymeric materials for use as fluorescent tracers. Potentially reactive functional groups that are intrinsically present or that can be introduced into biomolecules and polymers include but are not limited to amines, thiols, alcohols, carboxylic acids, aldehydes, and ketones. Chemically reactive fluorescent reagents have been developed in this invention for modification of all of these functional groups under conditions of solvent, temperature and pH that usually do not destroy the biological activity of the modified biomolecule. None of the reagents previously described in the chemical or biochemical literature are recognized as possessing the appropriate combination of chemical reactivity, spectral properties, high water solubility, fluorescence yield and lack of pH sensitivity to make them optimum for simultaneous use with fluorescein at wavelengths shorter than 500 nm.

The new pyrenyloxy sulfonic acid derivatives that are the subject of this invention have the general structure below.

In this structure, $R_1$, $R_2$, $R_3$, and $R_4$ are chosen among the substituents hydrogen, halogen, alkyl, alkoxy, arylalkoxy, carboxyalkyl, carboxylalkoxy, aryl, sulfo, and acyl, alone or in combination and one, two or three of these groups is a sulfonic acid, a salt of a sulfonic acid or another readily ionized group which confers water solubility. Furthermore, at least one of the substituents has the structure —O—$R_5$ with its oxygen directly bonded to the pyrene ring system and with a carbon atom bonded to the oxygen. Such a substitutent is further modified to provide a chemically reactive functional group. The subsequent modifications include but are not limited to chemically reactive derivatives of carboxylic acids such as succinimidyl esters, acyl azides, and acid halides, or other reactive groups that include acrylamides, alkyl and aryl azides, anhydrides, halides, sulfonate esters, amine and hydrazine derivatives, alcohols, haloacetamides, isothiocyanates and isocyanates. Several examples of derivatives that have the chemical structures and properties claimed by this invention and the precursors that are used in their synthesis are listed in Table 2.

TABLE 2
EXAMPLES OF SUBSTITUENTS OF NEW PYRENYLOXY SULFONIC ACID DYES

| Compound | $R_1$ | $R_2$ | $R_3$ | $R_4$ |
|---|---|---|---|---|
| 1 | $OCH_2CO_2CH_3$ | $SO_3Na$ | $SO_3Na$ | $SO_3Na$ |
| 2 | $OCH_2CO_2H$ | $SO_3Na$ | $SO_3Na$ | $SO_3Na$ |
| 3 | $OCH_2CONH(CH_2)_2NH_2$ | $SO_3Na$ | $SO_3Na$ | $SO_3Na$ |
| 4 | $OCH_2CONH(CH_2)_5NH_2$ | $SO_3Na$ | $SO_3Na$ | $SO_3Na$ |
| 5 | $OCH_2CONH$-Dextran-$NH_2$ | $SO_3Na$ | $SO_3Na$ | $SO_3Na$ |
| 6 | $OCH_2CONH(CH_2)_2NHCOCH_2Cl$ | $SO_3Na$ | $SO_3Na$ | $SO_3Na$ |
| 7 | $OCH_2CONH(CH_2)_5NHCOCH_2I$ | $SO_3Na$ | $SO_3Na$ | $SO_3Na$ |
| 8 | $OCH_2CO_2$-succ.[a] | $SO_3Na$ | $SO_3Na$ | $SO_3Na$ |
| 9 | $OCH_2CON_3$ | $SO_3Na$ | $SO_3Na$ | $SO_3Na$ |
| 10 | $OCH_2CONH(CH_2)_2OH$ | $SO_3Na$ | $SO_3Na$ | $SO_3Na$ |
| 11 | $OCH_2CONHNH_2$ | $SO_3H$ | $SO_3H$ | $SO_3H$ |
| 12 | $OCH_2CONHNH_2$ | $SO_3Na$ | $SO_3Na$ | $SO_3Na$ |
| 13 | $OCH_2CONHNH_2$ | $SO_3NH_4$ | $SO_3NH_4$ | $SO_3NH_4$ |
| 14 | $OCH_2CONH(CH_2)_2NHCOCH(CH_2)_3\overline{N}$-t-BOC | $SO_3Na$ | $SO_3Na$ | $SO_3Na$ |
| 15 | $OCH_2CONH(CH_2)_5NHCOCH(CH_2)_3\overline{N}$-t-BOC | $SO_3Na$ | $SO_3Na$ | $SO_3Na$ |
| 16 | $OCH_2CONH(CH_2)_5CN$ | $SO_3Na$ | $SO_3Na$ | $SO_3Na$ |
| 17 | $OCH_2CONH(CH_2)_2NHCOCH(CH_2)_3\overline{NH}.(CF_3CO_2H)$ | $SO_3Na$ | $SO_3Na$ | $SO_3Na$ |
| 18 | $OCH_2CONH(CH_2)_5NHCOCH(CH_2)_3\overline{NH}.(CF_3CO_2H)$ | $SO_3Na$ | $SO_3Na$ | $SO_3Na$ |
| 19 | $OCH_2CONH(CH_2)_5NHCOCH:CH_2$ | $SO_3Na$ | $SO_3Na$ | $SO_3Na$ |
| 20 | $OCH_2CONH(CH_2)_5NHCO(C_6H_4)N_3$ | $SO_3Na$ | $SO_3Na$ | $SO_3Na$ |
| 21 | $OCH_2CO_2CH_3$ | $OCH_2CO_2CH_3$ | $SO_3Na$ | $SO_3Na$ |
| 22 | $OCH_2CO_2CH_3$ | $OH$ | $SO_3Na$ | $SO_3Na$ |
| 23 | $OCH_2CO_2H$ | $OCH_2CO_2H$ | $SO_3Na$ | $SO_3Na$ |
| 24 | $OCH_2CO_2H$ | $OH$ | $SO_3Na$ | $SO_3Na$ |

[a]Succ. indicates a succinimidyl ester.

Chemically reactive derivatives of fluorophores have wide utility as tracers. This invention describes methods for preparation of pyrenyloxy sulfonic acid dyes that incorporate carboxylic acids and esters, amines, hydrazides, halides, alcohols and aldehydes and their subsequent modification to give chemically reactive reagents that can be coupled to other molecules for use as fluorescent tracers. Some of the reactive functional groups of the pyrenyloxy sulfonic acid dyes that have been prepared and the functional groups with which they are commonly reactive are listed in Table 3. The tabulation is not meant to be inclusive of chemical reactivity since with the appropriate choice of solvent, temperature and catalysts, other functional groups can be made to react and the listed functional groups can be made to react with other reactive sites.

TABLE 3

| REACTIVE FUNCTION | REACTIVE SITES |
|---|---|
| succinimidyl esters | amines, thiols |
| anhydrides | amines, alcohols |
| acyl azides | amines, thiols |
| isocyanates | amines, thiols, alcohols, phenols |
| isothiocyanates | amines, thiols, alcohols, phenols |
| hydrazines | aldehydes, ketones, acid derivatives |
| amines | carboxylic acids, halides, aldehydes and ketones |
| haloacetamides | thiols, imidazoles, phenols, amines |

TABLE 3-continued

| REACTIVE FUNCTION | REACTIVE SITES |
|---|---|
| alcohols | acid derivatives |
| halides | alcohols, amines, thiols, carboxylic acids |
| imido esters | amines |
| azides | photoaffinity reagents |
| sulfonate esters | alcohols, amines |
| acrylamides | olefins |
| maleimides | thiols, amines |

Figure 1:
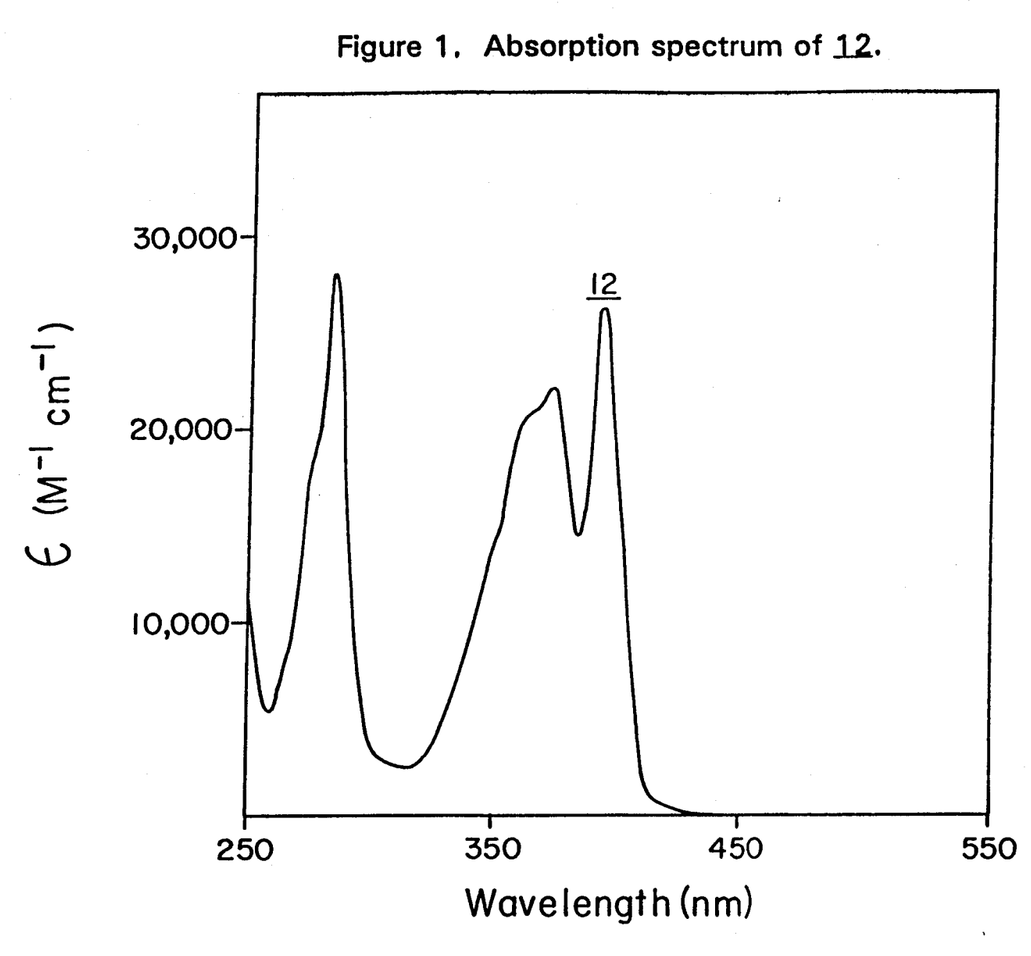
Figure 2:
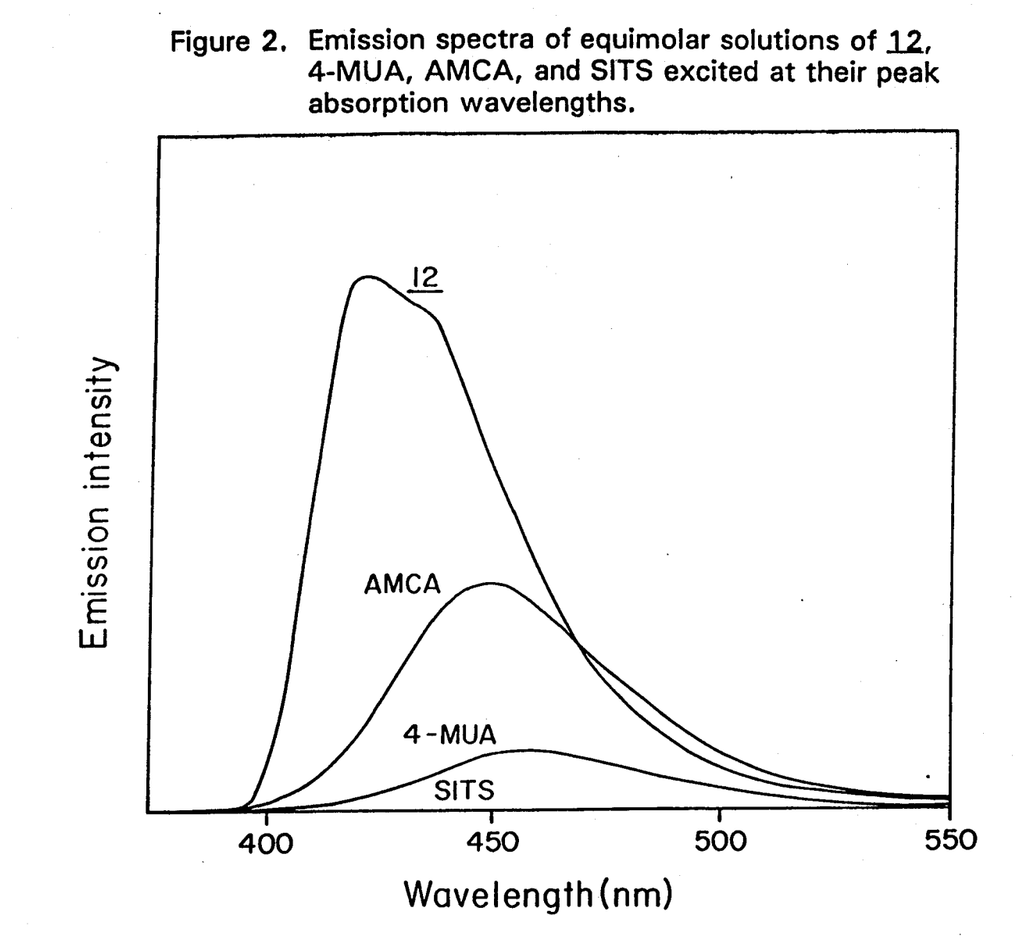
Figure 2. Emission spectra of equimolar solutions of 12, 4-MUA, AMCA, and SITS excited at their peak absorption wavelengths.
Figure 3:
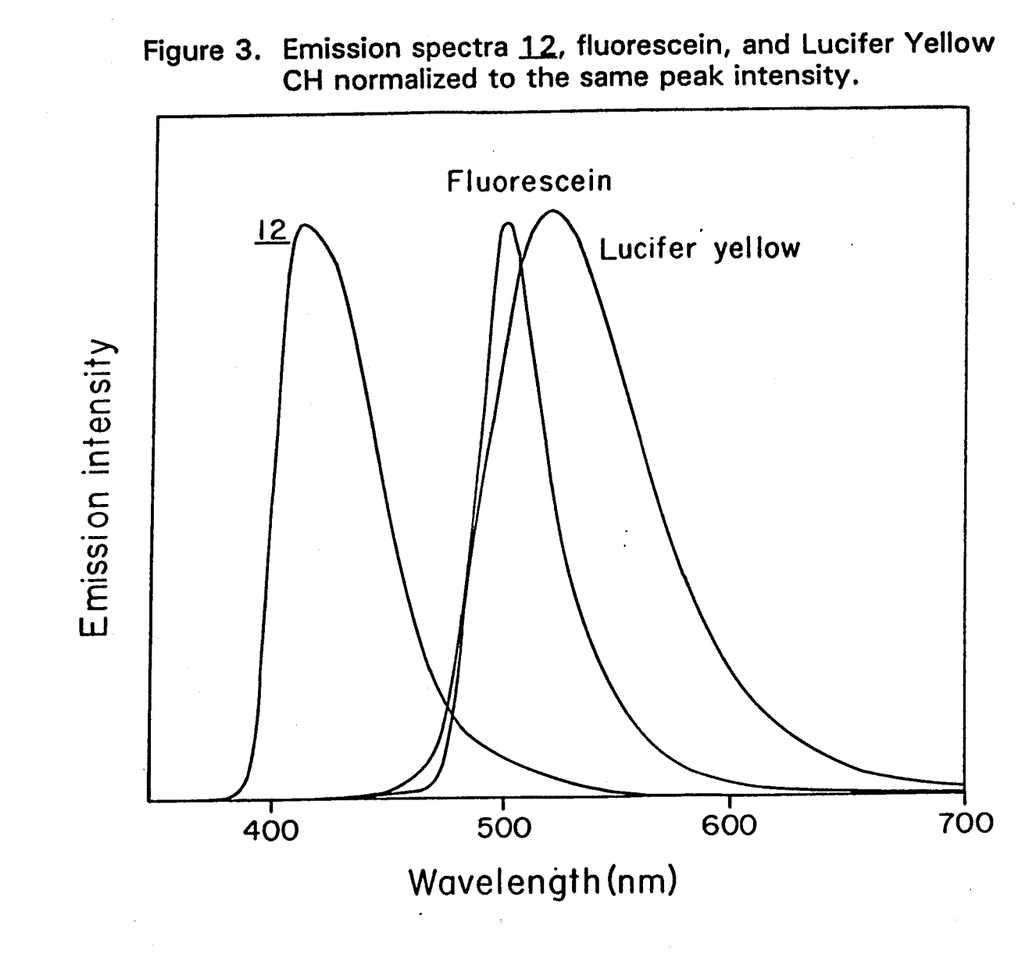
Figure 3. Emission spectra 12, fluorescein, and Lucifer Yellow CH normalized to the same peak intensity.
Figure 4:
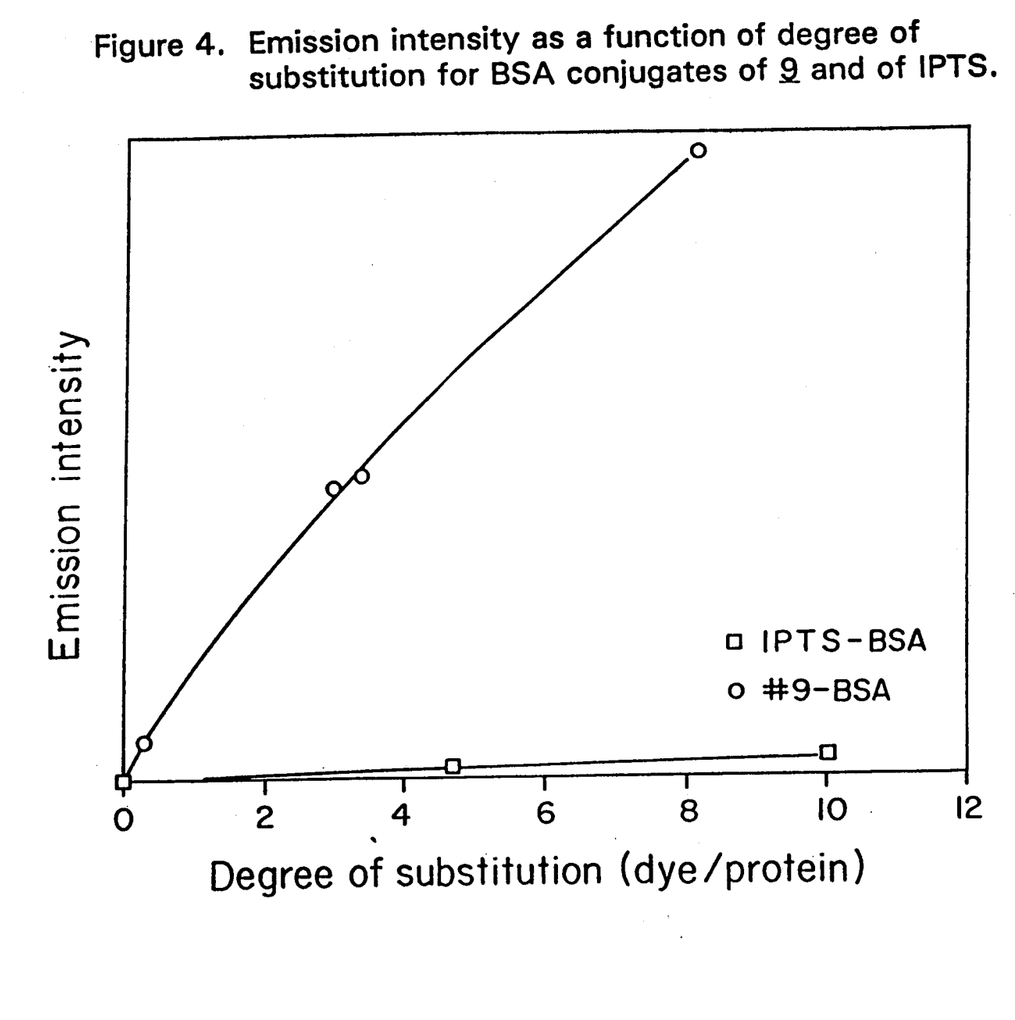
Figure 4. Emission intensity as a function of degree of substitution for BSA conjugates of 9 and of IPTS.
Figure 5:
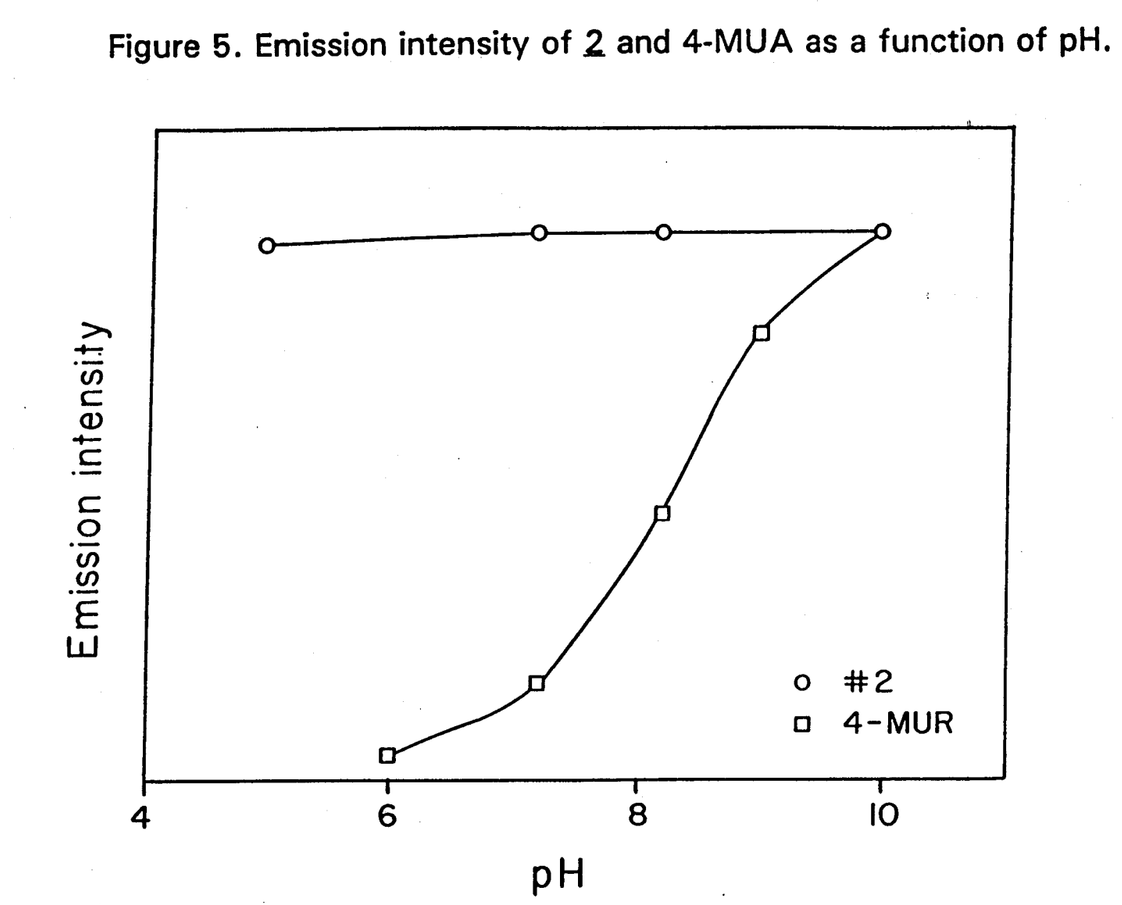
Figure 5. Emission intensity of 2 and 4-MUA as a function of pH.

The absorption spectrum of compound 12 is shown in FIG. 1. Emission spectra for equimolar solutions of chemical 12 from Table 2 versus 4-MUA, AMCA and SITS are given in FIG. 2. Obvious are the over twofold greater fluorescence intensity, significantly narrower emission spectral width and smaller Stokes' shift of the pyrenyloxy sulfonic acid dye. The narrower spectral width makes the dyes particularly valuable for applications requiring multiple dyes such as flow cytometry, DNA sequencing [Smith, et at. (1985)] and multiparameter microscopy. The utility of the objects of this invention in multiparameter applications is illustrated in FIG. 3. This figure shows the normalized emission spectra of compound 12, fluorescein, and Lucifer Yellow CH. Chemical 12 exhibits emission which is well resolved from the emission bands of both these widely used dyes. The extinction coefficients for the pyrenyloxy sulfonic acid dyes are generally greater than 25,000 $cm^{-1}M^{-1}$ and the quantum yields of the dyes in aqueous solution are generally above 0.5. In FIG. 4, the emission intensities of bovine serum albumin (BSA) conjugates of the pyrene isothiocyanate IPTS are compared to the BSA conjugates of compound 9. In this case, the conjugates of 9 are approximately thirtyfold more fluorescent than conjugates of IPTS. The subject dyes show only minor spectral shifts and intensity changes between water, methanol, and ethanol and have absorption and emission spectra that lack significant pH dependence between pH 6 and 10, as illustrated in FIG. 5. Table 4 lists the approximate spectral properties of a number of the dyes and intermediates that are the subject of this invention.

TABLE 4
SPECTRAL PROPERTIES OF NEW PYRENYLOXY SULFONIC ACID DYES[a]

| Compound | Abs Max (nm) | $\epsilon$ ($10^{-3} M^{-1} cm^{-1}$) | Em Max (nm) | Emission Band-width (nm) | Emission at 514 nm (% of max) |
|---|---|---|---|---|---|
| 2[b] | 403 | 27.0 | 430 | 52 | 5.8 |
|  | 374 | 19.8 |  |  |  |
| 3 | 399 | 26.4 | 423 | 50 | 4.9 |
|  | 378 | 21.2 |  |  |  |
| 4[b] | 398 | 27.6 | 422 | 50 | 3.9 |
|  | 377 | 22.8 |  |  |  |
| 5 | 400 | — | 423 | 50 | 4.5 |
|  | 378 | — |  |  |  |
| 10 | 399 | 26.6 | 423 | 50 | 3.3 |
|  | 377 | 21.7 |  |  |  |
| 11 | 399 | 25.1 | 423 | 51 | — |
|  | 377 | 20.7 |  |  |  |
| 12[c] | 399 | 27.5 | 423 | 50 | 3.9 |
|  | 377 | 22.9 |  |  |  |
| 13 | 399 | 28.0 | 423 | 50 | 3.8 |
| 14[b] | 376 | 23.3 |  |  |  |
|  | 399 | 26.9 | 422 | 49 | 2.8 |
|  | 378 | 21.2 |  |  |  |
| 15 | 399 | 23.0 | 423 | 50 | 3.0 |
|  | 377 | 18.4 |  |  |  |
| 16 | 399 | 30.0 | 423 | 49 | 3.0 |
|  | 377 | 24.3 |  |  |  |
| 19 | 399 | 26.3 | 423 | 49 | 2.9 |
|  | 378 | 20.8 |  |  |  |
| 20 | 400 | 24.8 | 424 | 50 | 3.5 |
|  | 378 | 18.8 |  |  |  |
| 21 | 396 | 24.5 | 447 | 55 | 13.0 |

[a] In 50 mM aqueous potassium phosphate buffer at pH 8.0
[b] Quantum yield greater than 0.90 in water
[c] Quantum yield = 0.54 in 50 mM phosphate buffer at pH 8.0

EXPERIMENTAL

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The following synthetic examples illustrate how one of ordinary skill in the art could synthesize a variety of chemically reactive derivatives containing the desired fluorophore that are the subject of this invention. The methods outlined are intended to be illustrative and not to define or limit the possible methods of dye synthesis. It is also to be recognized that the specific compounds described herein are included for the purpose of clearly demonstrating the nature of the invention and do not exhaust the structural and chemical variations which are also considered to fall within the scope of this invention. It is to be understood that certain changes and modifications which are apparent to one skilled in the art are included in the purview and intent of this invention. Inclusion of spectral and other characterization of some of the synthetic products and intermediates in Tables 2 and 4 is intended to facilitate comparison and confirmation of products by one skilled in interpretation of spectral techniques and not to specifically define limitations or absolute values for physical properties of the materials.

A general scheme for synthesis of several pyrenyloxy sulfonic acid dyes that are or can be modified to have the desired chemical reactivity or chemical substituents falling within the scope of this invention is illustrated below. The general method consists of condensation of an alkylating reagent such as an alkyl halide or appropriately substituted alkyl halide, in the presence of a base with a substituted or unsubstituted pyrene sulfonic acid having a hydroxyl on the 1,3,6 or 8-position to give an alkoxy intermediate such as 1.

Frequently, there are a number of alternative routes whose choice depends primarily on the availability (or ease of synthesis) of the reactants, solvents and equipment. Suitable bases for the initial alkylation step include but are not limited to bicarbonate, carbonate, diisopropylethylamine and triethylamine. Suitable substituents on the alkylating reagent include but are not limited to substituted or unsubstituted alkyl, cycloalkyl, arylalkyl and aryl derivatives. Pyrenyloxy sulfonic acid products may be modified in subsequent reactions by known chemical techniques including but not limited to esterification, sulfonation, nitration, alkylation, acylation, and halogenation. Furthermore, the substituents can in some cases be further modified to introduce chemically reactive functional groups that are understood to fall within the scope of this patent. Examples of methods that are suitable for preparation of selected members of this new class of reactive dyes are given in the examples outlined below. It is recognized that variations in the synthetic methods and reactants are possible that would fall within the scope and intent of this invention.

Examples of the preparation of reactive pyrenyloxy sulfonic acids:

I. Methyl 1,3,6-trisulfo-8-pyrenyloxyacetate, trisodium salt (1)

To a refluxing mixture of 26.2 g 8-hydroxypyrene-1,3,6-trisulfonic acid, trisodium salt in 1.7 l. methanol, 29 g methyl 2-bromoacetate and 18 g diisopropylethylamine were added in three portions over five hours. After refluxing for an additional three hours, the mixture was allowed to cool, filtered and evaporated under reduced pressure. The crude product obtained from the filtrate was stirred in 500 ml isopropyl alcohol for 30 min. and collected by filtration. After drying over potassium hydroxide for two days under vacuum, 28.7 g light yellow powder was obtained. A sample of the dye was purified by chromatography over lipophilic Sephadex using water for elution.

II. 1,3,6-Trisulfo-8-pyrenyloxyacetic acid, trisodium salt (2)

A solution of 6 g 1 in 20 ml water containing 0.4 g sodium hydroxide was warmed to 60° C. and stirred for 15 min. The solution was cooled to room temperature and acidified with 0.5 ml concentrated hydrochloric acid. Isopropyl alcohol (30 ml) was added to the resulting slurry and the solid was collected to give 4.6 g yellow powder after air drying. A sample of the dye was purified by chromatography over lipophilic Sephadex using water for elution.

III. 1,3,6-Trisulfo-8-pyrenyloxyacetamido-1-(2-aminoethane), trisodium salt (3)

To a hot solution of 5.01 g 1 in 100 ml methanol, 10 ml ethylenediamine was added in one portion. The mixture was refluxed for 3.5 hours, then cooled to 4° C. for two hours. The solid was collected by filtration and dried under vacuum to give 2.95 g yellow powder. The filtrate was evaporated and the resulting residue was triturated with 25 ml methanol. The solid was collected and dried to give an additional 1.24 g yellow powder. A sample of the dye was purified by chromatography over lipophilic Sephadex using water for elution.

IV. 1-(1,3,6-Trisulfo-8-pyrenloxyacetamido)-(5-aminopentane), trisodium salt (4)

To a solution of 1.0 g 1 in 50 ml methanol, 2 ml cadaverine was added. The mixture was refluxed for three hours, cooled and evaporated under reduced pressure. The residue was stirred for 30 min. in 100 ml isopropyl alcohol and the solid was collected. The crude product was purified by chromatography over lipophilic Sephadex using water for elution and product containing fractions were combined and lyophilized to give 0.83 g yellow powder.

V. 1,3,6-Trisulfo-8-pyrenyloxyacethydrazide, trisodium salt (12)

To a solution of 3 g 1 in 150 ml methanol, 2 ml anhydrous hydrazine was added and the mixture was refluxed overnight. The mixture was cooled to 4° C. for two hours and the solid was collected by filtration. After washing with methanol and drying, 2.3 g yellow powder was obtained. A sample of the dye was purified by chromatography over lipophilic Sephadex using water for elution. HPLC of a solution of 12 in water and a solution of 12 with one drop of acetone in water showed that 12 reacted to form a new product in the presence of acetone.

VI. 1,3,6-Trisulfo-8-pyrenyloxyacethydrazide, free sulfonic acid (11) and triammonium salt (13)

To 15 ml Dowex 50W-X12 (20 meq/ml) ion exchange resin that had been washed repeatedly with 1:20 concentrated hydrochloric acid:water followed by repeated washing with water was added 150 mg 12 in 25 ml water. The mixture was stirred gently for four hours and filtered. The resin was washed twice with 25 ml water. The combined filtrates were divided into two portions. One portion was lyophilized to give the free acid 11. The other portion was made distinctly basic with concentrated ammonium hydroxide and lyophilized to give the ammonium salt 13.

VII. 1,3,6-Trisulfo-8-pyrenyloxyacetyl azide, trisodium salt (9)

A solution of 100 mg 12 in 10 ml water was acidified with 2 drops of concentrated hydrochloric acid and cooled in an ice bath. A solution of sodium nitrite in water (1.0 ml, 0.013 g/ml) was added to the cold suspension. After stirring for 30 min., the ice bath was removed and the mixture was allowed to warm to room temperature. After stirring 15 min., an additional 1.0 ml of sodium nitrite solution was added. The mixture was stirred 10 min longer and then poured into 100 ml isopropyl alcohol. The precipitate was collected and washed with tetrahydrofuran to give 56 mg tan powder.

VIII. 1,3,6-Trisulfo-8-pyrenyloxyacetamido-dextranamine (5)

To a solution of 100 mg aminodextran (average molecular weight=70,000 g/mol, 38 amines/mol) in 5 ml dimethylsulfoxide, was added 12 mg 8. After stirring overnight, the mixture was diluted to approximately 50 ml and dialyzed against 3×4 l. 2% sodium sulfate in water then 3×4 l. water. The solution of dextran was lyophilized to give 90 mg light yellow powder. The degree of substitution was determined by comparing the molar absorptivity of the conjugate to the molar absorpitivity of compound 12. The dextran was found to contain approximately 13 moles of dye per 70,000 g of dextran.

IX. N-(1,3,6-Trisulfo-8-pyrenyloxyacetyl)-N'-(iodoacetyl)-1,5-pentanediamine, trisodium salt (7)

To a solution of 100 mg 4 and 4 drops diisopropylethylamine in 2 ml dimethylsulfoxide 120 mg p-nitrophenyl iodoacetate was added. After 30 min. the mixture was precipitated with chloroform and the solid collected by centrifugation to give 70 mg yellow powder. HPLC of a solution of 3.1 mg 7 in 3.00 ml 10 mM tetrabutylammonium phosphate and a solution of 2.0 mg 7 and one drop 2-mercaptoethanol in 3.0 ml 10 mM tetrabutylammonium phosphate showed complete conversion of 7 to a new product in the presence of 2-mercaptoethanol.

X. N-(1,3,6-Trisulfo-8-pyrenyloxyacetyl)-N'-(4-azidobenzoyl)-1,5-pentanediamine, trisodium salt (20)

To a solution of 70 mg 4 in 2 ml dimethylsulfoxide and 4 drops diisopropylethylamine was added 100 mg succinimidyl 4-azidobenzoate. After stirring overnight, the mixture was poured into 20 ml chloroform and the product collected by centrifugation. The crude product was purified by chromatography over lipophilic Sephadex using water for elution and product containing fractions were combined and lyophilized to give 37 mg yellow powder.

XI.
N-(1,3,6-Trisulfo-8-pyrenyloxyacetyl)-N'-(N-t-butoxycarbonyl-L-prolyl)-1,2-ethanediamine, trisodium salt (14)

A solution of 100 mg N-t-BOC-L-proline, succinimidyl ester in 1.5 ml dimethylformamide was added to a solution of 100 mg 3 and 4 drops 20% (w/v) sodium hydroxide in 3 ml water. After stirring for 30 min., the mixture was evaporated. The crude product was purified by chromatography over lipophilic Sephadex using water for elution and product containing fractions were combined and lyophilized to give 80 mg yellow powder.

XII. Dimethyl 1,3-disulfo-6-carboxymethoxy-8-pyrenyloxyacetic acid, disodium salt (21)

A solution of 100 mg 6,8-dihyroxypyrene-1,3-disulfonic acid, disodium salt, 10 ml methanol, 1 ml methyl 2-bromoacetate and 1 ml diisopropylethylamine was refluxed for 1 hour. The mixture was cooled and evaporated. The residue was washed with chloroform and acetone. The crude product was purified by chromatography over lipophilic Sephadex using water for elution and product containing fractions were combined and lyophilized to give 73 mg yellow powder.

XIII. Methods for characterization of the pyrenyloxy sulfonic acid dyes.

Stock solutions were prepared by accurately weighing and dissolving 5-10 mg samples of the compounds in 2.000 ml water. A 10 µl aliquot of the stock solution was diluted into 2.00 ml of 50 mM potassium phosphate buffer at pH 8.0. Absorbance solutions were prepared by further diluting 200 µl of the diluted stock solution to 2.000 ml with 50 mM potassium phosphate buffer at pH 8.0. Absorption data was collected on an IBM Model 9420 UV/Visible Spectrophotometer and extinction coefficients were determined by standard Beer's Law calculations.

Uncorrected fluorescence data was obtained on a Perkin-Elmer Model 650-40 Fluorescence Spectrophotometer equipped with a Perkin-Elmer/Hitachi 057 X-Y Recorder using a ten- to twentyfold dilution of the absorbance solutions. Fluorescence of the pyrenyloxy sulfonic acid dyes was determined for the reactive dyes and for their conjugates with model compounds by dissolving the dye at a concentration above $1 \times 10^{-8}$ M in an appropriate solvent such as water, methanol, ethanol, or dimethylsulfoxide and measurement of the fluorescence in a suitable instrument, such as a fluorescence spectrometer or fluorescence microscope or flow cytometer. Results of the spectral determination for some of the dyes are tabulated in Table 4. Fluorescence could also be observed for the dyes in solution by visual inspection with illumination by a suitable source that emits light at wavelengths of less than 420 nm.

An estimate of the quantum yield of the dyes relative to quinine sulfate (quantum yield = 0.55 in 1N sulfuric acid) was obtained by integrating the emission spectrum of the dye excited at the same wavelength and optical density as the standard. Spectral properties of these dyes are tabulated in Table 4.

The purity of the dyes was determined by HPLC analysis of 5 µl aliquots of solutions containing 0.33-1.0 mg/ml of the compounds dissolved in 5 mM tetrabutylammonium phosphate buffer (pH 7.5). Samples were eluted from a 150×4.6 mm Supelcosil LC-8-DB (5 µm) column with a gradient of 5 mM tetrabutylammonium phosphate buffer (pH 7.5) and acetonitrile (0-60% acetonitrile in 30 min.) at a flow rate of 2 ml/min. and an initial pressure of 1700 psi. Samples were detected by absorbance at 400 nm and purity was calculated by integration of this absorbance. Results of these analyses are summarized in Table 5. The structural identity of the products was determined by 300 MHz $^1$H NMR and the chemical shifts obtained are listed in Table 6. The spectroscopic data and chemical reactivity of the compounds were consistent with the structural assignments reported here.

TABLE 5

| HPLC OF NEW PYRENYLOXY SULFONIC ACID DYES | | |
| --- | --- | --- |
| Compound | Retention Time (min) | Purity (%)[a] |
| 1 | 10.74 | 90.7 |
| 2 | 9.32 | >97 |
| 3 | 7.98 | >97 |
| 4 | 8.77 | >97 |
| 7 | 10.33 | 71.7 |
| 10 | 9.38 | >97 |
| 12 | 8.96 | >97 |
| 13 | 8.91 | >97 |
| 14 | 12.64 | >97 |
| 15 | 11.93 | >97 |
| 16 | 11.30 | >97 |
| 17 | 9.68 | >97 |
| 18 | 10.50 | >97 |
| 19 | 10.50 | >97 |
| 20 | 11.38 | >97 |
| 21 | 13.51 | >97 |

[a]Purity was calculated by integration of the areas of product and impurity peaks as a function of absorbance at 400 nm.

TABLE 6

| $^1$H NMR OF PYRENYLOXY SULFONIC ACID DYES | |
| --- | --- |
| Compound | Chemical Shifts (ppm), Multiplicity, and Coupling Constants (Hz) |
| 1 | 3.76, s-3H; 5.01, s-2H; 8.06, s-1H; 8.58, d-1H(J=9.6Hz); 8.90, d-1H(J=9.9Hz); 8.94, d-1H(J=9.9Hz); 9.04, d-1H(J=9.9Hz); 9.15, s-1H |
| 2 | 4.95, s-2H; 8.19, s-1H; 8.90, d-1H(J=9.9Hz); 8.93, d-1H(J=9.9Hz); 9.02, d-1H(J=9.9Hz); 9.10, d-1H(J=9.9Hz); 9.14, s-1H |
| 3 | 2.99, t-2H(J=6Hz); 3.40, t-2H(J=6Hz); 4.62, s-2H; 7.93, s-1H; 8.40, d-1H(J=9.6 Hz); 8.81, d-1H(J=9.9Hz); 8.87, d-1H(J=9.6Hz); 8.95, d-1H(J=9.9Hz); 9.11, s-1H |
| 4 | 0.61, m-2H; 1.08, m-2H; 1.15, m-2H; 2.28, t-2H(J=7.5Hz); 2.92, t-2H(J=6.3Hz); 4.69, s-2H; 7.97, s-1H; 8.46, d-1H(J=9.6Hz); 8.88, d-1H(J=9.9Hz); 8.93, d-1H(J=9.9Hz); 9.01, d-1H(J=9.6Hz); 9.14, s-1H |
| 10 | 3.38, m-2H; 3.64, m-2H; 4.91, s-2H; 8.01, s-1H; 8.50, d-1H(J=9.9Hz); 8.84, d-1H(J=9.6Hz); 8.90, d-1H(J=9.6Hz); 8.98, d-1H(J=9.6Hz); 9.12, s-1H |
| 13 | 4.95, s-2H; 7.91, s-1H; 8.32, d-1H(J=9.6Hz); 8.81, d-2H(J=9.3Hz); 8.95, d-1H(J=9.9Hz); 9.08, s-1H |

TABLE 6-continued

¹H NMR OF PYRENYLOXY SULFONIC ACID DYES

| Compound | Chemical Shifts (ppm), Multiplicity, and Coupling Constants (Hz) |
|---|---|
| 16 | 0.82, m-2H; 1.21, m-4H; 1.87, t-2H(J=7.2Hz); 3.07, t-2H(J=6.3Hz); 4.90, s-2H; 8.07, s-1H; 8.65, d-1H(J=9.6Hz); 8.89, d-1H(J=9.9Hz); 8.96, d-1H(J=9.6Hz); 9.02, d-1H(J=9.9Hz); 9.114, s-1H |
| 19 | 2.20, t-2H; 3.30, m-2H; 3.37, m-2H; 3.65, t-2H; 4.60, m-2H; 4.90, s-2H; 5.30, m-2H; 5.50, m-1H; 8.09, s-1H; 8.68, d-1H(J=9.9Hz); 8.86, d-1H(J=9.9Hz); 8.96, d-1H(J=9.6Hz); 9.01, d-2H(J=10.2Hz); 9.09, s-1H |

XIV. Determination of the chemical reactivity of the dyes.

The chemical reactivity of the dyes that are the subject of this invention was determined by incubation of the reactive derivatives in aqueous, methanolic, or dimethylsulfoxide solution with model compounds. Their reactivity was demonstrated by thin layer chromatography in a solvent that separated the reactive dye from its products with visual detection of the fluorescence emission or by HPLC with photometric detection. It was demonstrated that 1-aminobutane reacts to form a new product with 9, that aminodextran reacts with 9 to give 5, that bovine serum albumin, protein A, avidin and streptavidin react with 9 to give fluorescent protein conjugates, that 2-mercaptoethanol reacts with 6 and 7, that 4 reacts with succinimidyl acrylate and succinimidyl 4-azidobenzoate to form 19 and 20, respectively, that 3 and 4 react with succinimidyl N-t-BOC-L-proline to give 14 and 15, respectively, that chloroacetic anhydride reacts with 3, that acetone reacts with 12, and that N-hydroxysuccinimide reacts with 2 in the presence of N,N'-dicyclohexylcarbodiimide to give an ester. Furthermore, it was demonstrated that the esters such as 1 can react with hydrazine to give hydrazides such as 12 and with amines to give amides such as 3, 4, 10 and 16.

What is claimed is:

1. A fluorescent dye having the structure:

wherein
(a) at least one of $R_1$, $R_2$, $R_3$, and $R_4$ has the structure —O—$R_5$ wherein $R_5$ includes a chemically reactive functional group selected from the group consisting of —$CH_2C(O)OCH_3$, —$CH_2C(O)OH$, —$CH_2CON_3$, —$CH_2CONHNH_2$, and —$CH_2CONH(CH_2)_nNH_2$ where n is an integer from 1 to 10;
(b) at least one of $R_1$, $R_2$, $R_3$, and $R_4$ is selected from the group consisting of sulfonic acid and alkali salts of sulfonic acid; and
(c) all other of $R_1$, $R_2$, $R_3$, and $R_4$ are selected from the group consisting of a hydrogen and a hydroxyl group.

2. A fluorescent dye as recited in claim 1 wherein $R_1$ has the structure —$OCH_2C(O)OCH_3$ and $R_2$, $R_3$, and $R_4$ have the structure —$SO_3X$, wherein X is an alkali metal.

3. A fluorescent dye as recited in claim 1 wherein $R_1$ has the structure —$OCH_2C(O)OH$ and $R_2$, $R_3$, and $R_4$ have the structure —$SO_3X$, wherein X is an alkali metal.

4. A fluorescent dye as recited in claim 1 wherein $R_1$ has the structure —$OCH_2CON_3$ and $R_2$, $R_3$, and $R_4$ have the structure —$SO_3X$, wherein X is an alkali metal.

5. A fluorescent dye as recited in claim 1 wherein $R_1$ has the structure —$OCH_2CONHNH_2$ and $R_2$, $R_3$, and $R_4$ have the structure —$SO_3X$, wherein X is an alkali metal.

6. A fluorescent dye as recited in claim 1 wherein $R_1$ has the structure and $R_2$, $R_3$, and $R_4$ have the structure —$SO_3X$, wherein X is an alkali metal.

7. A fluorescent dye as recited in claim 1 wherein $R_1$ has the structure —$OCH_2CONH(CH_2)_nNH_2$, where n is an integer from 1 to 10, and $R_2$, $R_3$, and $R_4$ have the structure —$SO_3X$, wherein X is an alkali metal.

8. A fluorescent dye as recited in claim 1 wherein $R_1$ has the structure —$OCH_2C(O)OH$, $R_2$ is a hydroxyl group, and $R_3$ and $R_4$ have the structure —$SO_3X$, wherein X is an alkali metal.

9. A fluorescent dye as recited in claim 1 wherein $R_1$ and $R_2$ have the structure —$OCH_2C(O)OH$ and $R_3$ and $R_4$ have the structure —$SO_3X$, wherein X is an alkali metal.

* * * * *

UNITED STATES PATENT AND TRADEMARK OFFICE
CERTIFICATE OF CORRECTION

PATENT NO. : 5,132,432
DATED : 07/21/92
INVENTOR(S) : R.P. Haugland and J.E. Whitaker It is certified that error appears in the above-identified patent and that said Letters Patent is hereby corrected as shown below:

Column 1, line 5, above FIELD OF INVENTION, insert --This invention was made with government support under grant number 37347 awarded by the National Institutes of Health. The government has certain rights in this invention.

Signed and Sealed this

First Day of March, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.    : 5,132,432
DATED         : July 21, 1992
INVENTOR(S)   : Haugland et al.

It is certified that error appears in the above-identified patent and that said Letters Patent is hereby corrected as shown below:

Column 16,
Line 14, should read -- -$\overline{CH_2C(O)ONCO(CH_2)_2C}O$ --

Signed and Sealed this

Fifth Day of November, 2002

*Attest:*

*Attesting Officer*

JAMES E. ROGAN
*Director of the United States Patent and Trademark Office*